United States Patent [19]

Asahi et al.

[11] Patent Number: 5,545,538
[45] Date of Patent: Aug. 13, 1996

[54] METHOD OF PRODUCING VITAMIN B12 USING RHIZOBIUM COBALAMINOGENUM FERM BP-4429

[75] Inventors: Satoru Asahi, Takatsuki; Takahiko Yano, Ikeda; Muneharu Doi, Takarazuka, all of Japan

[73] Assignee: Takeda Chemical Industries, Ltd., Osaka, Japan

[21] Appl. No.: 318,555

[22] Filed: Oct. 5, 1994

[30] Foreign Application Priority Data

Oct. 6, 1993 [JP] Japan .................................. 5-250603

[51] Int. Cl.$^6$ .............................. C12N 1/00; C12N 1/20; C12P 1/04; C12P 19/42
[52] U.S. Cl. .......................... 435/86; 435/170; 435/252.2; 435/878
[58] Field of Search .................... 435/86, 170, 252.2, 435/878

[56] References Cited

FOREIGN PATENT DOCUMENTS 49-15796  4/1974  Japan .
WO91/11518  8/1991  WIPO .

OTHER PUBLICATIONS

Shemakhanova et al., "Selection of the active Rhizobium strains according . . .", 1970, abst.
Troitskaya et al. "Influence of Rhizobium japonicum strains and cobalt . . ." 1986, abst.
Troitskaya, "Effect of cultivation conditions of soy–bean on vitamin . . ." 1983, abst.
Rodynyuk et al., "Vitamin B–12 accumulation . . .," 1974, abst.
Rodynuk et al., "Bgroup vit. level in nodules . . . ," 1973, abst.
Elmerich et al., "Nicotinic acid requirement and degrada–tion by *Sesbania rhizobium* strain ORSS71", 1983, 281–84.
Abstract from obraz. Fiziol. AKT. Veshchestv Mikroorg., 1975 Rodynyuk et al., "Role of B vit(s) & a.a. in rel. betwn. symb. bact.".
Abstract from Izobreteniya, Roslyakova et al., 1992 (21), p. 103 "Improving growth of Rhizobium in . . .".
Chanova, "Release Of Vitamin B12 From Rh. Leguminosa–rum", Chemical Abstracts, vol. 89, No. 15, Oct. 9, 1978, p. 294, left column, No. 125 899u.
Samtsevich et al., "Production of Vitamin B12 By Rhizobial Bacteria Of Lupine", Chemical Abstracts, vol. 85, No. 17, Oct. 25, 1976, p. 279, left column, No. 119 366u.
Leiderman et al., "Vitamin B12 Synthesis By Rhizobium Phaseoli", Chemical Abstracts, vol. 82, No. 19, May 12, 1975, p. 251, right column, No. 121 470e.
KLIEWER et al., "Cobamide Coenzyme Contents of Soy–bean Nodules & Nitrogen Fixing Bacteria in Relation to Physiological Conditions", Plant Physiology, 38, 99–104 (1963).

*Primary Examiner*—David M. Naff
*Assistant Examiner*—Deborah K. Ware
*Attorney, Agent, or Firm*—Wenderoth, Lind & Ponack

[57] ABSTRACT

There is provided an economical, efficient and industrially useful method of producing vitamin $B_{12}$ which comprises cultivating a microorganism belonging to *Rhizobium cobalaminogenum* FERM BP-4429 which is capable of producing vitamin $B_{12}$ in a culture medium and recovering the vitamin $B_{12}$. The microorganism is isolated from soil and has no formation of acids from L-arabinose. Further, there are no straight chain fatty acids 21:1 or 19:0.

5 Claims, No Drawings

METHOD OF PRODUCING VITAMIN B12 USING RHIZOBIUM COBALAMINOGENUM FERM BP-4429

FIELD OF THE INVENTION

The present invention relates to a method of producing vitamin $B_{12}$ which has widely been used as an agent for treating pernicious anemia, nervous diseases, methylmalonic aciduria, etc., and feed additives for fowls and/or domestic animals.

BACKGROUND OF THE INVENTION

The industrial production of vitamin $B_{12}$ by chemical synthetic methods is difficult because of its complex structure. Fermentation processes using microorganisms have been used for its production.

It is reported that vitamin $B_{12}$ is produced by microorganisms belonging to the genera Streptomyces, Norcardia, Micromonospora, Aerobacter, Agrobacterium, Alcaligenes, Azotobacter, Bacillus, Clostridium, Corynebacterium, Escherichia, Flavobacterium, Mycobacterium, Pseudomonas, Propionibacterium, Proteus, Serratia, Streptococcus, Xanthomonas, Protaminobacter, Methanobacillus (E. J. Vandamme, Biotechnology of Vitamins, Pigments and Growth Factors, Elsevier Science Publisher LTD, 1989, 261–263), Arthrobacter (JP-A 52-94498), Klebsiella (JP-A 50-132186), Rhodopseudomonus (JP-A 60-16597), Butyribacterium (JP-A 62-44197), Pseudonocardia (JP-A 55-96091), Methanosarcina (JP-A 1-257490), Eubacterium (JP-A 62-44172), Acetobacterium (JP-A 62-122593), etc. Further, it is reported that vitamin $B_{12}$ is accumulated by microorganisms belonging to the genera Rhizobium meliloti, Rhizobium phaseoli, Rhizobium japonicum, Rhizobium trifolli and Rhizobium leguminosarum (Plant Physiology, 38, 99–104 (1963)).

Of the above microorganisms belonging to the genus Rhizobium, Rhizobium phaseoli and Rhizobium trifolli have been renamed Rhizobium leguminosarum (see Institute for Fermentation, Osaka, Japan, List of Cultures 1992 Microorganisms, 9th edition, p. 169). A part of Rhizobium japonicum has been renamed Rhizobium leguminosarum and the rest has been re-classified into Bradyrhizobium japonicum (see Institute for Fermentation, Osaka, Japan, List of Cultures 1992 Microorganisms, 9th edition, p. 169).

However, in general, microbial processes produce vitamin $B_{12}$ in very low yield. Further, some microorganisms can utilize limited carbon sources (methanol assimilating bacteria, etc.), need special cultivation conditions such as anaerobic conditions (propionibacteria, microorganisms belonging to the genus Acetobacterium, methane producing bacteria, etc.), need long cultivation because of their low growth rates (methane producing bacteria, propionibacteria, etc.), and therefore can be used for industrial production only under limited conditions. Thus, improved industrial methods of producing vitamin $B_{12}$ are desired.

OBJECTS OF THE INVENTION

The main object of the present invention is to provide an industrially useful, economical and efficient method of producing vitamin $B_{12}$.

This object as well as other objects and advantages of the present invention will become apparent to those skilled in the art from the following description.

SUMMARY OF THE INVENTION

To develop an efficient fermentative method of producing vitamin $B_{12}$ using as carbon sources glucose, sucrose, etc., which have generally and widely been used for fermentative processes, and using aerobic and agitating culture which is a generally and widely used fermentation condition, the present inventors have isolated the novel strain Rhizobium cobalaminogenum 27B74 having high capability of producing vitamin $B_{12}$ from soil in Hyogo prefecture, Japan. After further studies, the present invention has been completed based on the findings thus obtained.

The present invention provides a method of producing vitamin $B_{12}$ which comprises cultivating a microorganism belonging to Rhizobium cobalaminogenum which is capable of producing vitamin $B_{12}$ in a culture medium to produce vitamin $B_{12}$ and recovering the produced vitamin $B_{12}$.

The present invention also provides a microorganism belonging to Rhizobium cobalaminogenum which is capable of producing vitamin $B_{12}$.

The present invention also provides a microorganism Rhizobium cobalaminogenum 27B74 (FERM BP-4429).

DETAILED DESCRIPTION OF THE INVENTION

The term "vitamin $B_{12}$" used in the present invention includes all types of vitamin $B_{12}$ such as coenzyme-type vitamin $B_{12}$ (adenosylcobalamin, methylcobalamin (methyl-type cobalamin)), cyano-type vitamin $B_{12}$ (cyanocobalamin) and hydroxo-type vitamin $B_{12}$ (hydroxocobalamin).

The morphological characteristics, growth in various media and physiological characteristics of Rhizobium cobalaminogenum 27B74 (IFO 15543, FERM BP-4429) isolated from soil which has excellent capability of producing vitamin $B_{12}$ are as follows.

(A) Morphological characteristics (in the case of the growth at 28° C. for 24 hours in broth agar medium)

| | | |
|---|---|---|
| 1. | Shape of the cells: | Bacili |
| 2. | Size of the cells: | 0.5–0.8 μm × 1–2.8 μm |
| 3. | Spores: | None |
| 4. | Motility: Observed (in observation after the growth in broth liquid culture at 28° C. for 16 hours) | |
| 5. | Gram stain: | Negative |
| 6. | Acid fastness: | None |

(B) Growth in various media

| | | |
|---|---|---|
| 1. | Broth agar plate culture (in the case of the growth at 28° C. for 48 hours) | |
| | Shape: | Circular |
| | Protuberance: | high in the center |
| | Sheen: | None |
| | Verge: | Entire |
| | Color tone: | Cream |
| | Viscosity: | None |
| | Dispersive pigments: | None |
| 2. | Broth liquid culture (in the case of growth at 28° C. for 24 hours) | |
| | Growth: | Accompanied by opacification |
| | Liquid surface: | Membranous, No ring formation |
| | Precipitation: | Observed |
| | Color tone: | Cream |
| 3. | Broth agar slant culture | |
| | Growth: | Viscous |
| | Color tone: | Cream |

| | |
|---|---|
| Sheen: | Observed |
| Dispersive pigments: | None |
| 4. Litmus milk culture (in the case of the growth at 28° C. for 24 to 96 hours) | |
| Reaction: | Unchanged |
| Formation of gas: | None |
| (C) Physiological characteristics | |
| Reduction of nitrate: | + |
| Denitrification: | − |
| VP test: | − |
| Indole formation: | − |
| MR test: | − |
| Urease: | + |
| Oxidase: | + |
| Catalase: | + |
| Utilization of citric acid (Koser-Christensen medium): | + |
| Hydrolysis: | |
| Starch: | − |
| Casein: | − |
| DNA: | − |
| Tween 80: | − |
| Formation of pigments: | − |
| Decarboxylation test: | |
| Lysine: | − |
| Arginine: | − |
| Ornithine: | − |
| Utilization of inorganic nitrogen: | |
| Ammonium salt: | + |
| Nitrate: | + |
| Formation of 3-ketolactic acid: | − |
| Response to oxygen: | Aerobic |
| O–F test: | Oxidation |
| pH for the growth: | |
| Optimum: | 6.0–8.0 |
| Maximum: | 11.0 |
| Minimum: | 3.5 |
| Temperature for the growth: | |
| Optimum: | 28–35° C. |
| Maximum: | 41.0° C. |
| Minimum: | 10.0° C. |
| (D) Utilization of various saccharides | |
| L-arabinose: | − |
| D-xylose: | − |
| D-glucose: | + |
| D-mannose: | + |
| D-fructose: | − |
| D-galactose: | + |
| Maltose: | + |
| Sucrose: | + |
| Lactose: | + |
| Trehalose: | + |
| D-sorbit: | + |
| D-mannit: | + |
| Inosit: | + |
| Glycerin: | + |
| Starch: | − |
| Adonitol: | + |
| Cellobiose: | + |
| L-rhamnose: | + |
| Dulcitol: | + |
| L-sorbose: | − |
| Choline chloride: | + |
| D-mannitol: | + |
| D-mannose: | + |

The formation of gas or acids from the above saccharides was not observed after cultivation for 14 days.

The above characteristics were classified based on the description in Bergey's Manual of Systematic Bacteriology, 1st ed. (1984). As a result, these bacteria were found to be bacteria belonging to the genus Rhizobium. The GC content in the DNA of the bacteria was determined and found to be 63.4%. Extraction and analysis of quinone compounds showed that all of these bacteria had coenzyme Q-10. Analysis of the fatty acid composition showed that the bacterial cells contained 3-hydroxyfatty acids 14:0, 16:0 and 18:0 (the number of carbon atoms:the number of double bonds) as hydroxyfatty acids, and the ratio was 66:17:7. In addition, the cells contained straight-chain fatty acids 16:0, 18:0 and 18:1, and 18:1 was contained most. It has been known that many microorganisms belonging to the genus Rhizobium have bacterial cellular fatty acid composition as described above. However the characterized strain has different characteristics from those of known microorganisms belonging to the genus Rhizobium in that the characterized strain does not have straight-chain fatty acids 21:1 or 19:0 and no formation of acids from L-arabinose is observed. The DNA homology was analyzed according to the method of Ezaki et al. (Ezaki et al., International Journal of Systematic Bacteriology, 39, 224–229 (1989)) and compared with that of known stock strains of the genus Rhizobium. The results are as follows.

TABLE 4

| Strain | Consensus with 27B74 strain |
|---|---|
| Rhizobium fredii IFO 14780 | 6.7 |
| Rhizobium galegae IFO 14965 | 17.8 |
| Rhizobium huakuii IFO 15243 | 7.9 |
| Rhizobium leguminosarum IFO 14784 | 27.7 |
| Rhizobium loti IFO 13336 | 5.9 |
| Rhizobium meliloti IFO 14782 | 16.4 |
| Rhizobium tropici IFO 15247 | 11.8 |

The 27B74 strain had no homology as the same species with any of these strains. Therefore it is concluded that this strain is a novel species strain belonging to the genus Rhizobium, and this species is designated as *cobalaminogenum*. The IFO numbers are accession numbers to Institute for Fermentation, Osaka (IFO, 2-17-8, Juso-honmach, Yodogawa-ku, Osaka-shi, Osaka-fu, Japan), and the FERM BP numbers are accession numbers to National Institute of Bioscience and Human-Technology, Agency of Industrial Science and Technology (FRI, 1-3, Higashi 1 chome, Tsukuba-shi, Ibaraki-ken, Japan) under the Budapest Treaty.

*Rhizobium cobalaminogenum* 27B74 was deposited at IFO on Sep. 2, 1993 under the accession number IFO 15543 and at FRI on Sep. 29, 1993 under the accession number FERM BP 4429.

The vitamin $B_{12}$-producing bacteria thus obtained can be cultivated in a similar manner to that of cultivation of conventional microorganisms. That is, the medium to be used contains carbon sources, nitrogen sources, inorganic materials, metal salts, yeast extract, yeast cells, ribonucleic acids, and if necessary, nutrition sources such as amino acids and vitamins. Examples of carbon sources include carbohydrates such as glucose, sucrose, maltose, sorbitol, starch, saccharified starch solutions and syrup; various organic acids such as pyruvic acid, fumaric acid, malic acid and succinic acid; alcohols such as ethanol and methanol; and amines such as betaines, cholines and monoethanolamine. Examples of nitrogen sources include organic nitrogen sources such as peptone, corn steep liquor, soybean flour and urea; and inorganic nitrogen sources such as ammonium salts of sulfuric acid, nitric acid, carbonic acid, etc., ammonia gas and ammonia water. These carbon and nitrogen sources can be used alone or as mixtures thereof. Other nutrition sources are appropriately selected from yeast extract, yeast cells, ribonucleic acids, inorganic salts (e.g., calcium salts, magnesium salts, potassium salts, phosphates, etc.), amino acids and vitamins, and are used alone or as mixtures thereof. In addition, if necessary, antifoaming agents such as silicone oil, surfactants such as polyalkylene glycol ether, etc., can be added. Further, it is preferred that the medium contains a cobalt compound or a 5,6-dimethylbenzimidazole compound. These compounds produce a high yield of vitamin $B_{12}$ in the medium. Any cobalt compounds can be used so long as they are cobalt sources or cobalt precursors. Examples of the cobalt compound include cobalt halides (e.g., cobalt chloride, cobalt bromide, etc.), cobalt nitrate, cobalt sulfide, cobalt acetate, cobalt ammonium sulfate, cobalt carbonate, cobalt 4-cyclohexylbutyrate, cobalt 2-ethylhexanoate, cobalt hydroxide, cobalt phosphate, cobalt oxide and cobalt thiocyanate. Any 5,6-dimethyl benzimidazole compounds can be used so long as they are 5,6-dimethylbenzimidazole sources or its precursors. Examples of the 5,6-dimethylbenzimidazole compound include 5,6-dimethylbenzimidazole, nicotinamide, nicotinate adenine dinucleotide (NAD), nicotinamide adenine dinucleotide (NaAD), nicotinate mononucleotide (NaMN), nicotinamide adenine dinucleotide phosphate (NADP) and nicotinic acid.

The cultivation is normally carried out under aerobic conditions, for example, by shaking culture, aerobic and agitation submerged culture, etc. The pH of the medium is preferably in the range of about 4 to 9. When pH changes are observed during the cultivation, acids (e.g., sulfuric acid, hydrochloric acid, acetic acid, etc.), alkalis (e.g., calcium carbonate, sodium hydroxide, ammonia gas, ammonia water, etc.) can appropriately be added to maintain the preferred range of the pH. The cultivation temperature suitable for the growth of the microorganism to be used and the accumulation of vitamin $B_{12}$ is selected from the range of normally about 20° C. to 45° C. The cultivation is continued until the essentially maximum amount of vitamin $B_{12}$ is accumulated. Normally, cultivation for about 2 days to 10 days is sufficient for this purpose.

Like other bacteria, vitamin $B_{12}$-producing bacteria belonging to the genus Rhizobium cobalaminogenum can be mutated by irradiation of ultraviolet light, radiation, etc., single cell isolation, various mutagenesis treatments, etc., in a conventional manner. The mutants thus obtained and naturally occurring mutants need not be classified into different groups in view of their taxonomic characteristics compared with those of the original bacteria. Any of these microorganisms capable of producing vitamin $B_{12}$ can be used in the present invention.

Vitamin $B_{12}$ thus obtained and each component thereof can be separated from the culture broth and collected by known conventional separating and purifying means such as solvent extraction using phenol, butanol, etc., precipitation methods, chromatography using ion exchange resins, silica gel, activated charcoal, etc. (J. Florent and L. Ninet, Vitamin $B_{12}$ Microbial Technology, edited by H. J. Peppler and D. Perlman, Academic Press, N.Y., p. 497–519 (1979)).

For example, the culture broth is centrifuged to give bacterial cells. The pH is adjusted to about 5.0 using inorganic acids (e.g., hydrochloric acid, sulfuric acid, etc.) or organic acids (e.g., acetic acid, tartaric acid, etc.). Then, cyanide ions are added followed by heating to obtain cyano-type vitamin $B_{12}$, which is then extracted into an aqueous phase. To obtain methyl-type or coenzyme-type vitamin $B_{12}$, they are extracted from the bacterial cells with alcohols (e.g., ethanol, propanol, etc.), ketones (e.g., acetone, methyl ethyl ketone, etc.) by conventional methods in a dark place. The extraction of vitamin $B_{12}$ from the bacterial cells is advantageously carried out by optionally crushing the bacterial cells by conventional methods.

According to the present invention, vitamin $B_{12}$ can be produced economically and efficiently.

The following examples further illustrate the present invention in detail, but are not to be construed to limit the scope thereof. All the percent (%) and ratios in the examples are percent (%) by volume and ratios by volume, respectively, unless otherwise indicated.

EXAMPLE 1

A broth liquid medium (5 ml) containing 1% (by weight) sucrose was dispensed into tubes with cotton plugs and sterilized by heating. One loopful of Rhizobium cobalaminogenum 27B74 (IFO 15543, FERM BP-4429) grown on a broth agar medium at 30° C. for 3 days in advance was inoculated and cultivated at 30° C. for 24 hours with shaking. The medium (20 ml) having the composition in Table 5 was placed in a 200 ml flask, sterilized by heating, inoculated with the above culture (1.0 ml) and incubated at 30° C. for 6 days on a rotary shaker at 230 rpm.

The culture broth (1 liter) obtained in a similar manner to that described above was centrifuged to collect bacterial cells. The resulting cells were suspended in an acetic acid buffer to adjust the suspension to pH 5.0. KCN was added thereto to a final concentration of 100 μg/ml, and then the mixture was heated at 100° C. for 15 minutes. After cooling, the resulting precipitates were removed by centrifugation to obtain a vitamin $B_{12}$ extract solution. Vitamin $B_{12}$ in the solution was determined by high performance liquid chromatography (HPLC) using ODP-50 4.6×150 mm (manufactured by Asahi Chemical Industry Co., LTD., Japan) as the column and 40 mM ammonium acetate:acetonitrile=88:12 for the elution of vitamin $B_{12}$ from the column. The vitamin $B_{12}$ content in the eluate was determined by measuring the absorbance at 361 nm. The results showed that 22 μg/ml of vitamin $B_{12}$ formed in the above culture broth.

Then, the above vitamin $B_{12}$ extract solution was subjected to activated charcoal column to adsorb vitamin $B_{12}$. After washing the column with distilled water, the adsorbed materials were eluted with 40% acetone. The vitamin $B_{12}$ fractions were collected, concentrated under reduced pressure and subjected to Dowex (trade name) 50 column chromatography. After washing the column with water, the adsorbed materials were eluted with 50 mM sodium acetate buffer (pH 6.5). The vitamin $B_{12}$ fractions were collected, neutralized, and then subjected to activated charcoal column chromatography again. After washing the column with distilled water, the adsorbed materials were eluted with 40% acetone. The vitamin $B_{12}$ fractions were collected and concentrated under reduced pressure. Vitamin $B_{12}$ was crystallized by adding acetone to the residue to give crystals of vitamin $B_{12}$ (cyano-type)(16.5 mg).

TABLE 5

| | |
|---|---|
| Sucrose | 30.0 g |
| $KH_2PO_4$ | 0.2 g |
| Corn steep liquor | 30.0 g |
| $MgSO_4.7H_2O$ | 0.2 g |
| Choline chloride | 10.0 g |
| 5,6-dimethylbenzimidazol | 0.025 g |
| $CoCl_2.6H_2O$ | 0.1 g |
| Tap water | 1 liter |
| pH | 7.0 |

EXAMPLE 2

To obtain each coenzyme-type vitamin $B_{12}$, the culture broth (1 L) obtained in Example 1 was centrifuged to obtain bacterial cells, the concentration of ethanol (containing no cyanide ions) was adjusted to 80% in a dark place, and the cells were extracted under heating at 80° C. for 20 minutes. Ethanol in the extract was evaporated under reduced pressure to obtain an aqueous solution. The solution was desalted using Sep-Pack C 18 (manufactured by Waters), and then coenzyme-type vitamin $B_{12}$ was identified by high performance liquid chromatography using Lichrospher RP 18 (5× 250 mm)(manufactured by Merck) as the column. The elution from the column was carried out by gradient method using 85 mM phosphoric acid (pH 3.0) and acetonitrile. The concentration of acetonitrile was changed from 0% (at the beginning of the elution) to 50% (25 minutes after the beginning of the elution). The content of the coenzyme-type vitamin $B_{12}$ in the eluate was determined by measuring the absorbance at 361 nm. The results showed that adenosylcobalamin (Ado-$B_{12}$)(18 µg/ml), methylcobalamin ($CH_3$-$B_{12}$)(2.5 µg/ml) and hydroxocobalamin (OH-$B_{12}$)(1.0 µg/ml) formed in the above culture broth.

COMPARATIVE EXAMPLE

Vitamin $B_{12}$ production using type strains of bacteria belonging to the genus Rhizobium In a similar manner to that described in Example 1, *Rhizobium meliloti* IFO 14782, *Rhizobium galegae* IFO 14965, *Rhizobium huakuii* IFO 15243, *Rhizobium leguminosarum* IFO 13337, *Rhizobium leguminosarum* IFO 14784, *Rhizobium loti* IFO 13336 and *Rhizobium tropici* IFO 15247 were cultivated at 30° C. for 6 days. The vitamin $B_{12}$ content in the extract of the resulting culture was determined using the method described in Example 1. The results are in Table 6.

TABLE 6

| Strain | IFO No. | Vitamin $B_{12}$ (µg/ml) |
| --- | --- | --- |
| *Rhizobium galegae* | IFO 14965 | 0.03 |
| *Rhizobium huakuii* | IFO 15243 | 0.06 |
| *Rhizobium leguminosarum* | IFO 13337 | 0.7 |
| *Rhizobium leguminosarum* | IFO 14784 | 0.7 |
| *Rhizobium loti* | IFO 13336 | 0 |
| *Rhizobium meliloti* | IFO 14782 | 0.01 |
| *Rhizobium tropici* | IFO 15247 | 0 |

What is claimed is:

1. A method of producing vitamin $B_{12}$ which comprises cultivating a biologically pure culture of a microorganism belonging to *Rhizobium cobalaminogenum* FERM BP-4429 which is capable of producing vitamin $B_{12}$ in a culture medium and recovering the produced vitamin $B_{12}$ from a culture broth.

2. A biologically pure culture of a microorganism belonging to *Rhizobium cobalaminogenum* FERM BP-4429 which is capable of producing vitamin $B_{12}$.

3. The method according to claim 1, wherein the culture medium contains a cobalt compound.

4. The method according to claim 3, wherein the cobalt compound is cobalt halide.

5. The method according to claim 1, wherein the culture medium contains a 5,6-dimethylbenzimidazole compound.

* * * * *